US010292624B2

United States Patent
Sabiston et al.

(10) Patent No.: US 10,292,624 B2
(45) Date of Patent: May 21, 2019

(54) METHOD AND SYSTEM FOR GENERATING A THREE-DIMENSIONAL SCAN OF AN OBJECT

(71) Applicant: VORUM RESEARCH CORPORATION, Vancouver (CA)

(72) Inventors: Robert Malcolm Sabiston, Vancouver (CA); Jeffrey David Chang, Vancouver (CA); Carl Saunders, North Vancouver (CA)

(73) Assignee: Vorum Research Corporation, Vancouver, B.C. (CA)

( * ) Notice: Subject to any disclaimer, the term of this patent is extended or adjusted under 35 U.S.C. 154(b) by 349 days.

(21) Appl. No.: 15/111,574

(22) PCT Filed: Jan. 19, 2015

(86) PCT No.: PCT/CA2015/000033
§ 371 (c)(1),
(2) Date: Jul. 14, 2016

(87) PCT Pub. No.: WO2015/109387
PCT Pub. Date: Jul. 30, 2015

(65) Prior Publication Data
US 2016/0331278 A1    Nov. 17, 2016

Related U.S. Application Data

(60) Provisional application No. 61/929,857, filed on Jan. 21, 2014.

(51) Int. Cl.
*A61B 5/00*     (2006.01)
*A61B 34/10*    (2016.01)
(Continued)

(52) U.S. Cl.
CPC .......... *A61B 5/1079* (2013.01); *A61B 5/0064* (2013.01); *A61B 5/107* (2013.01);
(Continued)

(58) Field of Classification Search
None
See application file for complete search history.

(56) References Cited

U.S. PATENT DOCUMENTS 6,744,537 B1 *    6/2004  Chiba ................ H04N 1/00687
                                                      358/404
7,940,260 B2     5/2011  Kriveshko
(Continued)

FOREIGN PATENT DOCUMENTS

| WO | 2009/063087 A2 | 5/2009 |
| WO | 2009/089126 A1 | 7/2009 |
| WO | 2012/115863 A2 | 8/2012 |

OTHER PUBLICATIONS

Basic, Goran, Authorized Officer, Canadian Intellectual Property Office, "International Search Report" in connection with related International Application No. PCT/CA2015/000033, dated Apr. 27, 2015, 4 pages.
(Continued)

*Primary Examiner* — Manav Seth
*Assistant Examiner* — David Perlman
(74) *Attorney, Agent, or Firm* — Kolisch Hartwell, P.C.

(57) ABSTRACT

A method and system for generating a three-dimensional scan of an object using a handheld scanner is disclosed. The method involves obtaining images of the object from a successive plurality of handheld scanner positions with respect to the object, and processing the images to generate a respective 3D frame for each of the plurality of handheld scanner positions. Each 3D frame includes data representing locations of a plurality of 3D points on a surface of the (Continued)

object. The method further involves comparing each successive 3D frame with at least one preceding 3D frame, determining whether a result of the comparison meets a correspondence criterion associated with generation of a 3D representation of the surface of the object, and initiating a recovery process when the correspondence criterion is not met.

36 Claims, 6 Drawing Sheets

(51) Int. Cl.
| | | |
|---|---|---|
| *A61B 5/107* | (2006.01) | |
| *G01B 11/25* | (2006.01) | |
| *G06T 17/10* | (2006.01) | |
| *G06T 7/521* | (2017.01) | |

(52) U.S. Cl.
CPC .......... *A61B 5/1077* (2013.01); *A61B 5/7221* (2013.01); *G01B 11/2513* (2013.01); *G06T 7/521* (2017.01); *G06T 17/10* (2013.01); *A61B 5/7455* (2013.01); *A61B 2034/108* (2016.02); *A61B 2560/0431* (2013.01); *A61B 2576/00* (2013.01); *G06T 2207/10004* (2013.01); *G06T 2207/30196* (2013.01)

(56) References Cited

U.S. PATENT DOCUMENTS

| | | | |
|---|---|---|---|
| 2002/0006217 A1 | 1/2002 | Rubbert et al. | |
| 2007/0171220 A1* | 7/2007 | Kriveshko | A61C 13/0004 345/419 |
| 2012/0062557 A1 | 3/2012 | Dillon et al. | |
| 2012/0300900 A1* | 11/2012 | Koivisto | A61B 5/0064 378/19 |
| 2013/0293684 A1 | 11/2013 | Becker et al. | |

OTHER PUBLICATIONS

Basic, Goran, Authorized Officer, Canadian Intellectual Property Office, "Written Opinion of the International Searching Authority" in connection with related International Application No. PCT/CA2015/000033, dated Apr. 27, 2015, 4 pages.

European Patent Office, "Extended European Search Report" in connection with related International Application No. EP15740156, dated Aug. 28, 2017, 7 pages.

* cited by examiner

METHOD AND SYSTEM FOR GENERATING A THREE-DIMENSIONAL SCAN OF AN OBJECT

BACKGROUND OF THE INVENTION

1. Field of the Invention

This invention relates generally to scanning objects and more particularly to generating a three-dimensional scan of an object using a handheld scanner.

2. Description of Related Art

Computer-aided design (CAD) systems may use a computer to modify a three-dimensional (3D) representation of an object. The CAD system may provide functionality for modifications that size, stretch, rotate, and otherwise make changes to the 3D representation. The modified representation may be used to produce instructions for controlling a computer-aided manufacturing (SAM) machine to fabricate a three-dimensional reproduction of the modified object.

For example, prostheses and orthoses are commonly produced from three-dimensional representations of a body part of a human or an animal. In some cases, generation of the prosthesis or orthosis is based on a 3D scan of the body part. A 3D scanner may be used to generate the 3D representation of the body part for use in the CAD system. One such scanner is the Spectra™ 3D handheld scanner produced by Vorum Research Corp. of Vancouver, BC, Canada. The Spectra 3D scanner projects a grid of light onto the body part of a patient or other object and captures images of the object while the operator moves the handheld scanner relative to the object. The images are transmitted to a scanner software program running on a computer, which processes the images to generate a set of 3D points representing surfaces of the object. For example, the object may be represented by a polygon mesh or triangular mesh having vertices that defined by 3D coordinates that lie on the surface of the object.

Handheld 3D scanners are convenient to use since additional equipment for mounting and moving the scanner is not required. However, operation by an inexperienced operator may result in images that are unsuitable for producing an accurate scan of the object. There remains a need for improved 3D scanning methods.

SUMMARY OF THE INVENTION

In accordance with one disclosed aspect there is provided a method for generating a three-dimensional scan of an object using a handheld scanner. The method involves obtaining images of the object from a successive plurality of handheld scanner positions with respect to the object, and processing the images to generate a respective 3D frame for each of the plurality of handheld scanner positions. Each 3D frame includes data representing locations of a plurality of 3D points on a surface of the object. The method further involves comparing each successive 3D frame with at least one preceding 3D frame, determining whether a result of the comparison meets a correspondence criterion associated with generation of a 3D representation of the surface of the object, and initiating a recovery process when the correspondence criterion is not met.

Determining whether the result of the comparison meets the correspondence criterion may involve determining whether 3D points associated with the 3D frame can be transformed to align with 3D points in the preceding 3D frame within a reference tolerance.

Initiating the recovery process may involve comparing a subsequent 3D frame with a 3D frame preceding the 3D frame that caused initiation of the recovery process, and resuming the scan of the object if a result of the comparison meets the correspondence criterion.

Resuming the scan of the object may involve resuming the scan without operator intervention.

The method may involve comparing the subsequent 3D frame with the 3D frame that caused initiation of the recovery process and may further involve one of retaining the frame if a result of the comparison meets the correspondence criterion, and discarding the frame if the result of the comparison does not meet the correspondence criterion.

The method may involve designating at least one preceding 3D frame as a reference frame and initiating the recovery process may involve comparing a subsequent 3D frame with a 3D frame preceding the 3D frame that caused initiation of the recovery process, and if a result of the comparison does not meet the correspondence criterion, comparing at least one of the subsequent 3D frame and the 3D frame that caused initiation of the recovery process with the reference frame and resuming the scan of the object if a result of the comparison with the reference frame meets the correspondence criterion.

Comparing at least one of the subsequent 3D frame and the 3D frame that caused initiation of the recovery process with the reference frame may involve comparing each of the subsequent 3D frame and the 3D frame that caused initiation of the recovery process with the reference frame.

Designating may involve designating at least one preceding 3D frame that meets a frame quality criterion as a reference frame the frame quality criterion is based on at least one of the presence of topological content of the frame, the presence of discernable features within the frame, and a data point density within the frame.

Designating may involve designating at least one preceding 3D frame as a reference frame in response to receiving operator input.

Designating may involve designating a plurality of preceding 3D frames as reference frames and comparing may involve comparing at least one of the subsequent 3D frame and the 3D frame that caused initiation of the recovery process with each of the plurality of reference frames.

Designating a plurality of preceding 3D frames as reference frames may involve designating a sufficient number of 3D frames as reference frames such that when the comparison result does not meet a correspondence criterion, at least one reference frame will be in view of the handheld scanner to permit the scan of the object to resume.

The method may further involve, if the result of the comparison between the at least one subsequent 3D frame and the 3D frame that caused initiation of the recovery process with the reference frame does not meet the reference criterion, providing feedback to the operator of the handheld scanner that a operator intervention is required.

Providing feedback to the operator may involve directing the operator to re-scan a portion of the object.

The method may involve obtaining further images of the object and processing the images to generate a further 3D frame for the re-scanned portion of the object and may further involve comparing the further 3D frame with a 3D frame preceding the 3D frame that caused initiation of the recovery process and if a result of the comparison meets the correspondence criterion, continuing the scan, and comparing the further 3D frame with the reference frame and if a result of the comparison meets the correspondence criterion, continuing the scan.

Providing feedback to the operator of the handheld scanner that an operator intervention is required may involve at least one of generating a visual warning, causing the handheld scanner to vibrate, displaying a warning 3D frame on a 3D frame display in view of the operator, and generating an audible warning.

The method may involve designating at least one preceding 3D frame as a reference frame and initiating the recovery process may involve generating operator feedback directing the operator to position the handheld scanner to obtain a further image from a location proximate the reference frame, processing the image to generate a 3D frame and comparing the 3D frame with the reference frame, determining whether a result of the comparison meets a correspondence criterion, and resuming the scan of the object when the correspondence criterion is met.

The method may involve designating at least one preceding 3D frame as a reference frame, and determining whether there has been an interruption in obtaining images of the object, and in response comparing a subsequent 3D frame with the reference frame and resuming the scan of the object if a result of the comparison with the reference frame meets the correspondence criterion.

Determining that there has been an interruption in obtaining images of the object may involve determining whether an elapsed time between successive images meets an interruption criterion.

The handheld scanner may include a single camera and obtaining images of the object may involve, for each of the plurality of handheld scanner positions projecting a pattern of light onto the surface of the object, causing the camera to capture an image of the surface while being illuminated by the pattern of light, causing the camera to capture a further image of the surface when not illuminated by the pattern of light, and comparing each successive 3D frame with at least one preceding 3D frame may involve using information provided by the further image to provide an estimate of the position of the handheld scanner for use in the comparison.

In accordance with another disclosed aspect there is provided a system for generating a three-dimensional scan of an object. The system includes a handheld scanner operable to generate images of the object from a successive plurality of handheld scanner positions with respect to the object. The system also includes a processor circuit operably configured to process the images to generate a respective 3D frame for each of the plurality of handheld scanner positions. Each 3D frame includes data representing locations of a plurality of 3D points on a surface of the object. The processor circuit is also operably configured to compare each successive 3D frame with at least one preceding 3D frame, determine whether a result of the comparison meets a correspondence criterion associated with generation of a 3D representation of the surface of the object, and initiate a recovery process when the correspondence criterion is not met.

The processor circuit may be operably configured to determine whether the result of the comparison meets the correspondence criterion by determining whether 3D points associated with the 3D frame can be transformed to align with 3D points in the preceding 3D frame within a reference tolerance.

The processor circuit may be operably configured to initiate the recovery process by comparing a subsequent 3D frame with a 3D frame preceding the 3D frame that caused initiation of the recovery process, and causing the scan of the object to resume if a result of the comparison meets the correspondence criterion.

The processor circuit may be operably configured to cause the scan of the object to resume without operator intervention.

The processor circuit may be operably configured to compare the subsequent 3D frame with the 3D frame that caused initiation of the recovery process and to cause one of retaining the frame if a result of the comparison meets the correspondence criterion, and discarding the frame if the result of the comparison does not meet the correspondence criterion.

The processor circuit may be operably configured to designate at least one preceding 3D frame as a reference frame and to initiate the recovery process by comparing a subsequent 3D frame with a 3D frame preceding the 3D frame that caused initiation of the recovery process, and if a result of the comparison does not meet the correspondence criterion, comparing at least one of the subsequent 3D frame and the 3D frame that caused initiation of the recovery process with the reference frame and causing the scan of the object to resume if a result of the comparison with the reference frame meets the correspondence criterion.

The processor circuit may be operably configured to compare each of the subsequent 3D frame and the 3D frame that caused initiation of the recovery process with the reference frame.

The processor circuit may be operably configured to designate at least one preceding 3D frame that meets a frame quality criterion as a reference frame, the frame quality criterion being based on at least one of the presence of topological content of the frame, the presence of discernable features within the frame, and a data point density within the frame.

The processor circuit may be operably configured to designate at least one preceding 3D frame as a reference frame in response to receiving operator input.

The processor circuit may be operably configured to designate the at least one preceding 3D frame by designating a plurality of preceding 3D frames as reference frames and to compare at least one of the subsequent 3D frame and the 3D frame that caused initiation of the recovery process with each of the plurality of reference frames.

The processor circuit may be operably configured to designate the plurality of preceding 3D frames as reference frames by designating a sufficient number of 3D frames as reference frames such that when the comparison result does not meet a correspondence criterion, at least one reference frame will be in view of the handheld scanner to permit the scan of the object to resume.

If the result of the comparison between the at least one subsequent 3D frame and the 3D frame that caused initiation of the recovery process with the reference frame does not meet the reference criterion, the processor circuit may be operably configured to provide feedback to the operator of the handheld scanner that a operator intervention is required.

The processor circuit may be operably configured to provide feedback to the operator by directing the operator to re-scan a portion of the object.

The handheld scanner may be operable to generate further images of the object and the processor circuit may be operably configured to process the images to generate a further 3D frame for the re-scanned portion of the object and to compare the further 3D frame with a 3D frame preceding the 3D frame that caused initiation of the recovery process and if a result of the comparison meets the correspondence criterion, continue the scan, and compare the further 3D frame with the reference frame and if a result of the comparison meets the correspondence criterion, continue the scan.

The processor circuit may be operably configured to provide feedback to the operator of the handheld scanner that an operator intervention is required by at least one of generating a visual warning, causing the handheld scanner to vibrate, displaying a warning 3D frame on a 3D frame display in view of the operator, and generating an audible warning.

The processor circuit may be operably configured to provide feedback to the operator by designating at least one preceding 3D frame as a reference frame and to initiate the recovery process by generating operator feedback directing the operator to position the handheld scanner to generate a further image from a location proximate the reference frame, processing the image to generate a 3D frame and comparing the 3D frame with the reference frame, determining whether a result of the comparison meets a correspondence criterion, and resuming the scan of the object when the correspondence criterion is met.

The processor circuit may be operably configured to designate at least one preceding 3D frame as a reference frame, and determine whether there has been an interruption in generating images of the object, and in response comparing a subsequent 3D frame with the reference frame and resuming the scan of the object if a result of the comparison with the reference frame meets the correspondence criterion.

The processor circuit may be operably configured to determine whether there has been an interruption in generating images of the object by determining whether an elapsed time between successive images meets an interruption criterion.

The handheld scanner may include a single camera, and the single camera may be operably configured to generate images of the object from the successive plurality of handheld scanner positions with respect to the object by projecting a pattern of light onto the surface of the object, capturing an image of the surface while being illuminated by the pattern of light, capturing a further image of the surface when not illuminated by the pattern of light, and the processor circuit may be operably configured to compare each successive 3D frame with at least one preceding 3D frame by using information provided by the further image to provide an estimate of the position of the handheld scanner for use in the comparison.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
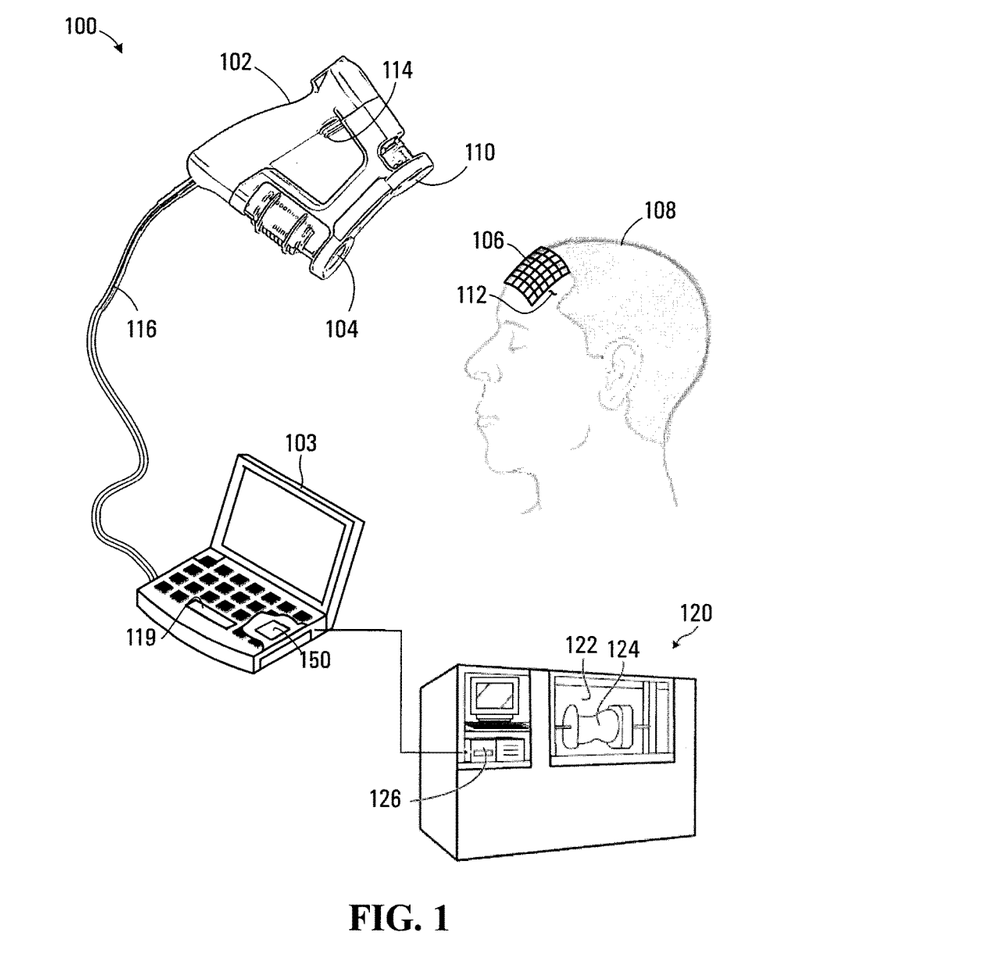
FIG. 1 is a perspective view of a scanning system for generating a scan of an object.

Referring to FIG. 1, a scanning system 100 is shown generally at 100. The scanning system 100 includes a handheld scanner 102 and a computer 103. The scanner 100 includes a projector 104 disposed to project a pattern of light 106 onto an object 108 (in this case a human head). In the embodiment shown the pattern of light 106 is a grid and the lines of the grid may be spatially or otherwise encoded to permit identification. The scanner 102 also includes a camera 110 disposed to capture images of a surface 112 of the object illuminated by the pattern 106. In this embodiment the scanner 102 includes an actuator button 114, which when depressed causes the projector 104 to be successively activated to project the pattern 106, and for each projection of the pattern an image is captured by the camera 110. The scanner 102 is interfaced to the computer 103 for downloading image data from the handheld scanner 102 to the computer. In this embodiment the interface is provided by a cable 116, but in other embodiments the scanner 102 may be wirelessly connected to the computer 103 for downloading image data.

The computer 103 includes a display 118 for displaying image data and a keyboard 119 for receiving operator input. The computer 103 also includes a processor circuit 150, operable to process the image data received on the cable 116 from the handheld scanner 102.

In the embodiment shown the scanning system 100 also includes a computer aided manufacturing (CAM) machine 120. The CAM machine 120 generally includes a machine tool portion 122 for machining the appliance. In this case the machined appliance is a mold 124 which is subsequently used to produce a final appliance by molding a thermoplastic or other material over the mold. The machined mold 124 has a shape defined by the computer representation of the mold and generally corresponds to the shape of the scanned body part, with alterations for fit, comfort, and/or support.

The CAM machine 120 also includes a controller 126 for controlling the machine tool portion 122 of the CAM machine. The controller 126 is in communication with the computer 103 for receiving a signal encoded with instructions operable to control the CAM machine 120 to produce the machined appliance 124. Alternatively the instructions may be output to a computer readable medium or memory for manual transfer to the CAM machine 120. An example of suitable CAM machines are the CANFIT-PLUS™ Carver and the CANFIT™ 6-Axis Carver, both produced by Vorum Research Corporation of British Columbia, Canada.

Figure 2:
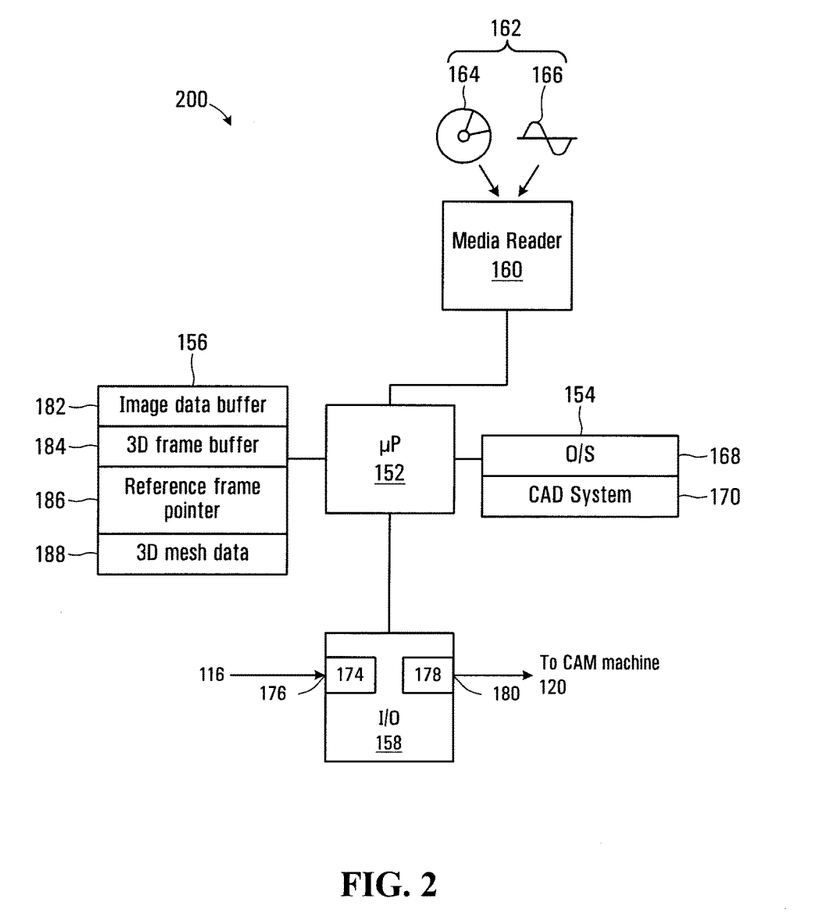
FIG. 2 is a processor circuit of the scanning system shown in FIG. 1.

The processor circuit 150 is shown in greater detail in FIG. 2. Referring to FIG. 2, the processor circuit 150 includes a microprocessor 152, a program memory 154, a random access memory (RAM) 156, an input/output port 158, and a media reader 160, all of which are in communication with the microprocessor 152. In one embodiment the microprocessor 152 may be a multi-core processor that facilitates parallel execution of certain tasks for reducing processing delays while performing the 3D scan.

Program codes for directing the microprocessor 152 to carry out various CAD functions are stored in the program memory 154, which may be implemented as a random access memory (RAM), and/or a hard disc drive (HDD), or a combination thereof. The program memory 154 includes a block of codes 168 for directing the microprocessor 152 to provide general operating system (O/S) functions, and a block of codes 170 for directing the microprocessor 152 to provide 3D scanning functions for generating the 3D scan of the object.

The media reader 160 facilitates loading program codes into the program memory 154 from a computer readable medium 162 such as a CD ROM disc 164, a flash memory (not shown), or a computer readable signal 166 such as would be received over a network such as the internet, for example.

The I/O 158 includes a scanner interface 174 having an input 176 for receiving signals encoded with image data received on the cable 116 from the handheld scanner 102. In one embodiment the scanner interface may be an IEEE 1394b interface (firewire). In other embodiments a USB interface such as a USB 3.0 may be used.

The I/O 158 also includes a second interface 178 having an output 180 for producing the signal encoded with shape representation data or carving instructions for controlling the CAM machine 120 to produce the appliance. The interfaces 174 and 178 may be universal serial bus (USB) or RS232 serial interfaces, for example.

The RAM 156 includes a plurality of storage locations, including an image data buffer 182 for storing images captured by the handheld scanner 102, a 3D frame buffer 184 for storing 3D frame data, a reference frame pointer location 186 for storing one or more pointers $n_{ref}$ designating a reference frame or frames, and a 3D mesh data store 188 for storing the resulting object scan.

Figure 3:
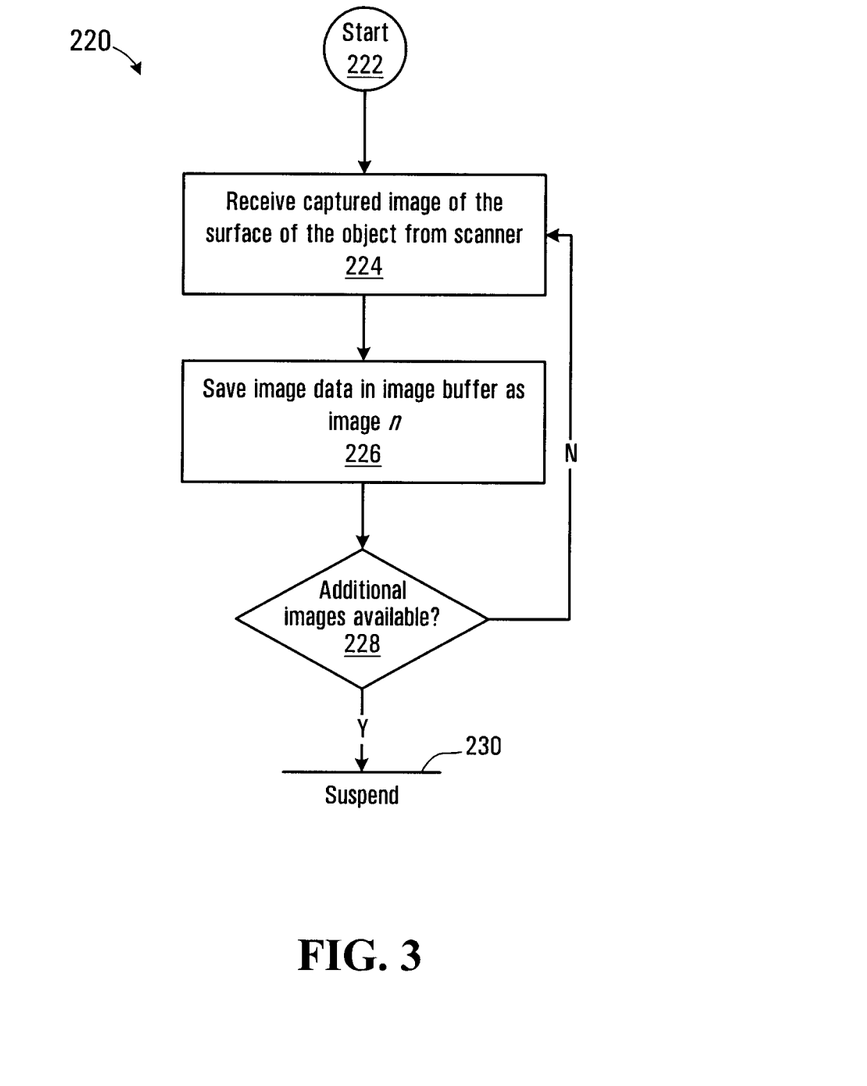
FIG. 3 is a process flowchart depicting blocks of code for directing the processor circuit shown in FIG. 2 to capture images for generating a 3D scan of an object.

Referring to FIG. 3, a flowchart depicting blocks of code for directing the processor circuit 150 to capture images for generating a 3D scan of an object is shown generally at 220. The blocks generally represent codes that may be read from the computer readable medium 162, and stored in the program memory 154, for directing the microprocessor 152 to perform various functions. The actual code to implement each block may be written in any suitable program language, such as C, C++ and/or assembly code, for example.

The process 220 starts at block 222 when operator depresses the actuator button 114. Block 224 directs the microprocessor 152 to receive a captured image of the surface 112 of the object 108 at the input 178 of the interface 174. As disclosed above, the handheld scanner 102 illuminates the object 108 with the grid of light 106, and causes the camera 110 to capture an image of the surface. In one embodiment, a further image may be captured without the grid of light 106 being projected on the surface. The images include image data representing the surface, for example in a JPEG compressed data format. Block 226 then directs the microprocessor 152 to save the image data in the image data buffer 182 of the RAM 156. In one embodiment, block 226 also directs the microprocessor 152 to assign an image pointer n, where n is an integer value for identifying the image.

The process then continues at block 228, which directs the microprocessor 152 to determine whether additional image data is available at the input 176 of the scanner interface 174. If at block 228 image data is available, the microprocessor 152 is directed back to block 224 and the blocks 224-228 of the process 220 are repeated. If at block 228 no further image data is available, the microprocessor 152 is directed to 230 and the process 220 is suspended. For example, when an operator of the scanner 102 pauses scanning by releasing the actuator button 114, the process 220 is suspended at 230 awaiting further image data from the scanner.

In embodiments where the microprocessor 152 is implemented using a multi-core processor, one or more of the processor cores may be dedicated to executing the process 220.

Figure 4:
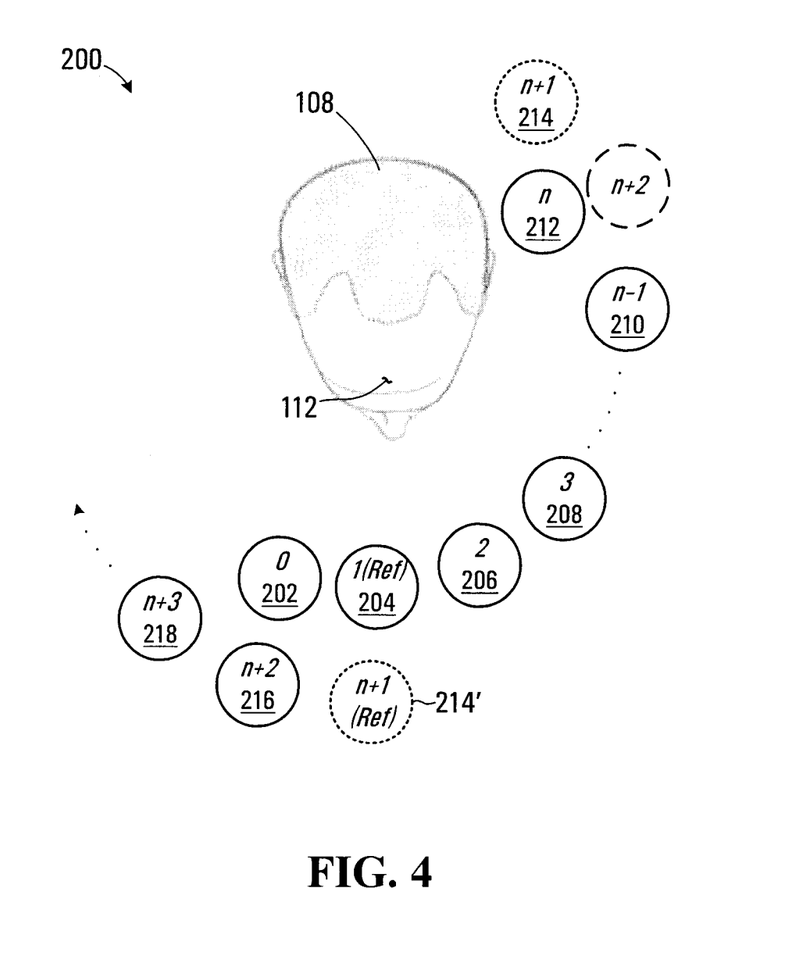
FIG. 4 is a schematic view of an object shown in FIG. 1 and a representation of a plurality of scanner positions with respect to the object.

Referring to FIG. 4, the object 108 is shown in top view and scanner positions 202-212 with respect to the object are illustrated using spaced apart circles to represent image captures at the successive plurality of scanner positions. Each successive scanner position 202-212 is spaced apart to provide an image capture of a portion of the surface 112 of the object 108 that at least partially overlaps the preceding captured image. In one embodiment, the handheld scanner 102 may be capable of capturing up to 15 images per second, thus providing for a substantial overlap between successive images taken at the scanner positions 202-212.

Figure 5:
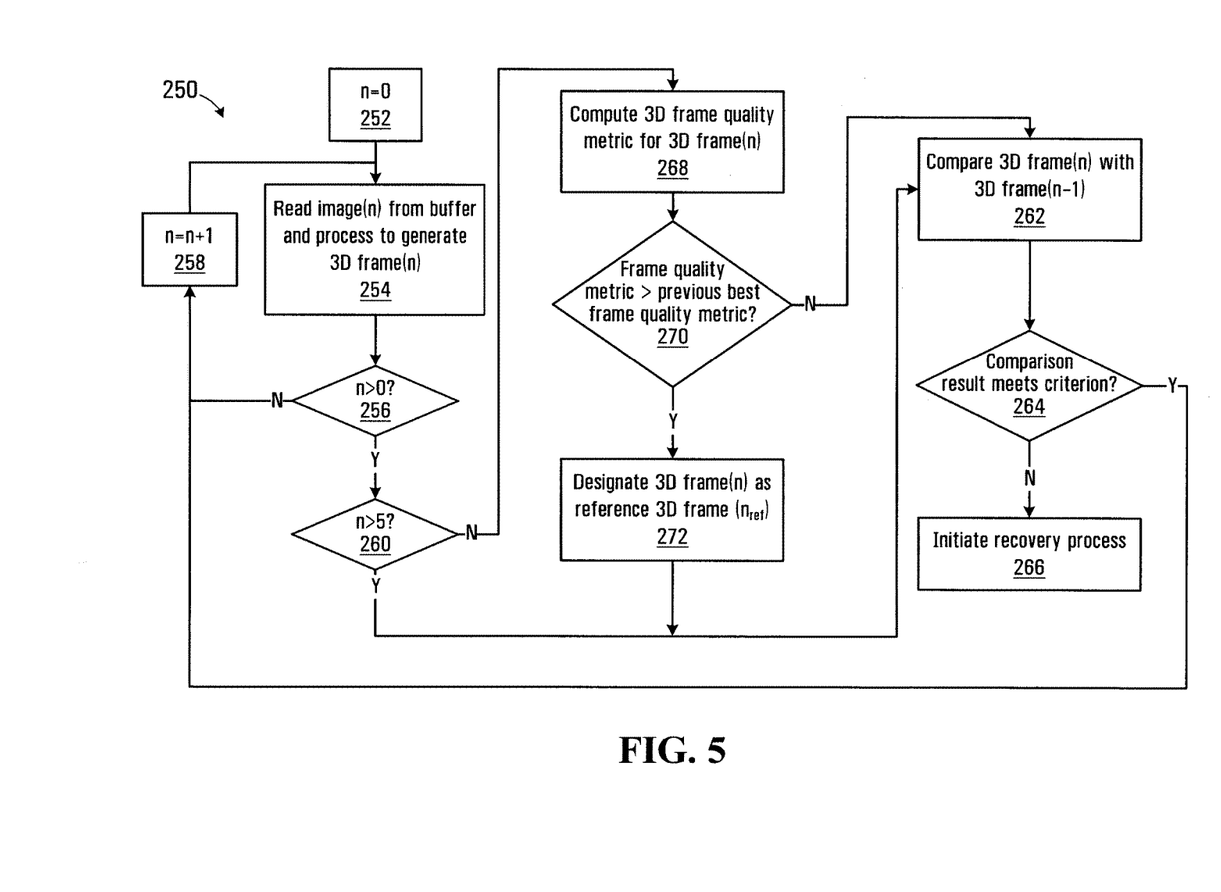
FIG. 5 is a process flowchart depicting blocks of code for directing the processor circuit of FIG. 2 to process the images captured in accordance with the process shown in FIG. 3.

Referring to FIG. 5, a process flowchart depicting blocks of code for directing the processor circuit 150 to process the images saved in the image data buffer 182 is shown generally at 250. The process begins at block 252, which directs the microprocessor 152 to set an image Pointer n to 0, for referencing the first image stored in the image data buffer 182. Block 254 then directs the microprocessor 152 to read the data for the image 0 and to generate a 3D frame based on the image data. When the captured surface 112 of the object 108 in the scene is non-planar, the surface distorts the grid of light 106 in the image and the 3D surface shape may be extracted using various structured-light principles and algorithms to generate a 3D frame including 3D surface coordinates. Known characteristics of the projected grid of light 106 may thus be used to identify points in the image in a coordinate frame associated with the handheld scanner 102, resulting in a 3D point cloud. The 3D point cloud may be further processed to generate a surface reconstruction, such as for example a polygon mesh or triangular mesh having a list of 3D coordinates of vertex locations each having an associated list of connections to other vertices. The processed 3D frame thus includes data representing locations of a plurality of 3D points on a surface of the object based on the captured image and is used for further processing. Block 254 also directs the microprocessor 152 to store the 3D frame data in the 3D frame buffer 184 of the RAM 156.

Block 256 then directs the microprocessor 152 to determine whether the image pointer is greater than zero, indicating that two or more images have been processed. If at block 256, only a single image has been processed, the microprocessor 152 is directed back to block 254 and a further image is processed. If at block 256, more then one image has already been processed, the microprocessor 152 is directed to block 260, which directs the microprocessor 152 to determine whether the image pointer is greater than 6, indicating that a reference frame has already been identified. In this embodiment a reference frame is selected from a first plurality of 3D frames, which in this case involves selecting the reference from the first 6 frames (i.e. frames 0-5).

If at block 260, n>5, a reference frame will have already been identified and the microprocessor 152 is directed to block 262. Block 262 directs the microprocessor 152 to compare the current 3D frame with the previous 3D frame (e.g. 3D frame(n−1)) and to generate a comparison result. In one embodiment, the comparison involves attempting to align the current 3D frame to at least one preceding frame (for example, frame 1 to frame 0). A common algorithm that is used to perform such an alignment is the Iterative Closest Point (ICP) algorithm. For example, an ICP algorithm may be implemented to transform 3D frame 1 to best align to the 3D frame 0 by iteratively revising a transformation (i.e. a combination of translation and rotation) to minimize the distances between point in the 3D frame 1 and planes in 3D frame 0. The ICP algorithm evaluates each transform iteration based on a mean squared error cost function, which may be used as a metric for comparing results of successive transformations. A final value of the mean squared error cost function also provides a measure for determining how well the transformed frame aligns to the preceding frame. In one embodiment the further image captured at block 224 of the process 220 (shown in FIG. 3) without the grid of light 106 being projected on the surface may be used to improve initial conditions for the ICP algorithm. For example, the further image may be analyzed to extract topological features that may be used to provide a rough alignment estimate for the alignment of the 3D frames, potentially improving the speed of convergence of the ICP algorithm.

The process 250 then continues at block 264, which directs the microprocessor 152 to determine whether a result of the comparison at block 262 meets a correspondence criterion associated with generation of a 3D representation of the surface of the object. For example, in one embodiment the criterion may be based on the ICP algorithm finding a transform that results in a final mean squared error cost function below a threshold value. Additional criteria may also be evaluated as part of the criterion at block 264. In one embodiment block 264 may also direct the microprocessor 152 to determine a degree of overlap between the frames. For example, if at least 500 points in 3D frame 1 lie within 0.5 mm of points in 3D frame 0, the frames may be considered to meet this additional criterion.

If at block 264, the correspondence criterion is met, then the microprocessor 152 is directed to save transformed coordinates for the 3D frame in the 3D mesh data store 188 of the RAM 156. The microprocessor 152 is also directed back to block 258, where the pointer n is incremented, and then back to block 254 for processing of the next image in the image data buffer 182.

When a successful comparison at block 264 is reached, the transformation provided by the ICP algorithm transforms the 3D frame into the same coordinate frame as the 3D frame that it was compared to. In the embodiment shown in FIG. 5, a first 3D frame (i.e. the 3D frame 0 at scanner position 202 in FIG. 4) is used to define a global coordinate system for the 3D object scan, and successive frames are transformed with reference to the global coordinate system for providing the 3D scan of the object. Transforms that convert coordinate systems for each 3D frame may be expressed as transform matrixes, which can be easily combined by matrix multiplication.

If at block 260, n≤5, a reference frame has not yet been identified and the microprocessor 152 is directed to block 268. Block 268 directs the microprocessor 152 to compute a frame quality metric. In one embodiment the frame quality metric involves determining whether the 3D frame meets an image quality criterion, which may be deduced from the amount of data in the 3D frame, an assessment of discernable features and/or topological content in the frame. In one embodiment the amount of data in the 3D frame is computed by dividing the number of vertices in the polygon mesh by the number of separate meshes in the 3D frame. Discernable features may be detected using an algorithm such as SURF (Speeded Up Robust Features), or SIFT (Scale-invariant feature transform), which are standard computer vision algorithms used to detect local features in images. Topological features may include local minimums or maximums of a convexity measurement calculated for the polygon mesh. Additional criteria may also be applied in determining whether a 3D frame is suitable for use as a reference frame.

The process then continues at block 270, which directs the microprocessor 152 to determine whether image quality of the current 3D frame is an improvement on the previous best frame quality based on the frame quality metric. If this is the case then the microprocessor 152 is directed to block 272, which directs the microprocessor 152 to designate the current 3D frame as the reference 3D frame. Referring to FIG. 4, a 3D frame taken at the scanner position 204 has been designated as the reference frame. Block 272 of the process 250 also directs the microprocessor 152 to save the pointer n for the 3D frame in the reference frame pointer location 186 of the RAM 156. If at block 270, the 3D frame does not meet the reference frame criteria, then the microprocessor 152 is directed to block 262 for processing of the 3D frame as described above.

The above embodiment has been described with reference to a single reference 3D frame. However, in other embodiments a plurality of reference frames may be detected and designated while scanning the object, such that when necessary the scan can resume from a closest reference frame. If a sufficient number of reference frames are designated, there will be a good likelihood that at least one reference frame is sufficiently in view to permit scanning to resume without the operator having to reposition the handheld scanner 102.

If at block 264, the correspondence criterion is not met, then the microprocessor 152 is directed to block 266, which directs the microprocessor to initiate a recovery process. In one embodiment block 266 may also direct the microprocessor 152 to generate a tone or other warning to inform the operator that the recovery process has been initiated. The correspondence criterion may not be met when the operator moves the scanner too fast, or the frame has poor quality (as described above in relation to block 268). Other conditions that may result in the correspondence criterion not being met may be when there is insufficient capture of surface of the object 108 and/or capture of background behind the object. In these cases, the inclusion of the 3D frame may result in an unsuccessful reconstruction of the surface 112 of the object 108. Referring back to FIG. 4, in the illustrated case the 3D frame at scanner position 212 is shown displaced with respect to the 3D frame at scanner position 210, as would occur if the operator moved the scanner too fast between capture of the images 210 and 212.

Alternatively, the correspondence criterion may also not be met if the operator were to deliberately discontinue scanning at image 212 and resume scanning again at image 214'. For example, the operator may release the actuator button 114 on the handheld scanner 102 at the image location 212, thus interrupting image capture, and then move the scanner to capture further images at the scanner positions 214', 216 and 218. In practice, the scan of the object 108 may proceed on the basis of several chains of successive images (such as the chain of images at scanner positions 202-210, and the chain of images at scanner positions 216', 2-6, 218 etc). Advantageously, scanning the object 108 as shown in FIG. 4 reduces potential accumulation of errors, as may occur if the chain of images 202-210 were to be continued around the back of the object. By periodically returning to the general location of the reference 3D frame at scanner position 204, and capturing further images such as the images 214', 216, and 218 from this location, the corresponding 3D frames may be referenced to the reference 3D frame thus potentially reducing scanning errors.

In embodiments where the microprocessor 152 is implemented using a multi-core processor, one or more of the processor cores may be dedicated to executing the process 250.

Figure 6:
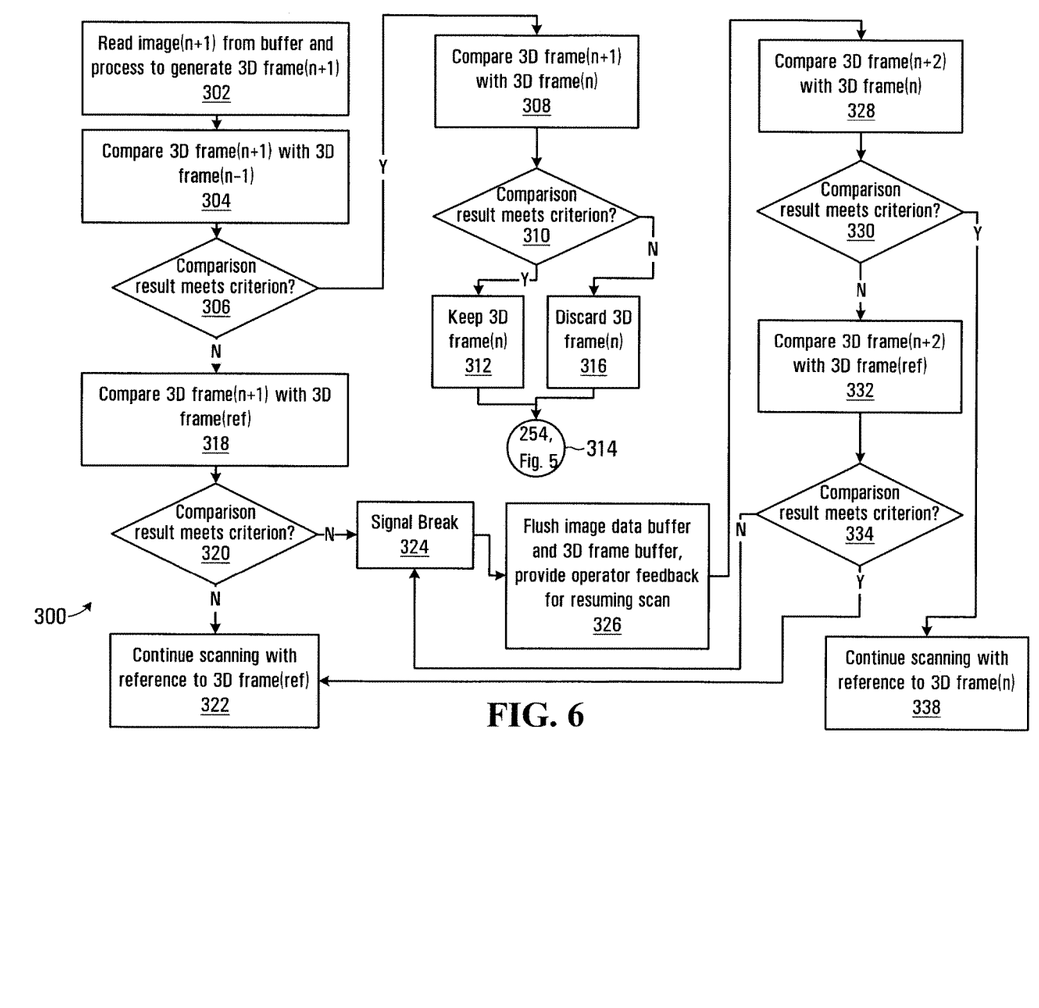
FIG. 6 is a process flowchart depicting blocks of code for directing the processor circuit of FIG. 2 to implement a recovery process in accordance with one embodiment of the invention.

Referring to FIG. 6, a process flowchart depicting blocks of code for directing the processor circuit 150 to implement a recovery process in accordance with one embodiment of the invention is shown at 300. The process 300 begins at block 302, which directs the microprocessor 152 to read a succeeding image n+1 from the image data buffer 182. Referring back to FIG. 4, in this example the image n (212) is the image that failed to meet the correspondence criterion and image n+1 (214) is the succeeding image. Block 304 then directs the microprocessor 152 to compare 3D frame n+1 with the preceding 3D frame n−1 (at scanner position 210), which was the last 3D frame that met the correspondence criterion. If at block 306 the result of the comparison meets the correspondence criterion, the microprocessor 152 is directed to block 308.

Block 308 then directs the microprocessor 152 to compare 3D frame n+1 with the frame n (at scanner position 212), i.e. the current frame. If at block 310 the result of the comparison meets the correspondence criterion, the microprocessor 152 is directed to block 312, which directs the microprocessor to keep the 3D frame n. If at block 310 the result of the comparison does not meet the correspondence criterion, the microprocessor 152 is directed to block 314, which directs the microprocessor to discard the 3D frame n. Block 306 thus first determines whether the next frame in sequence (frame n+1) is able to align to frame n−1 which would permit the scan to continue. Blocks 308-316 then determine whether the frame n should be kept or discarded based on whether the succeeding frame n+1 is able to align to frame n. Whether the frame n is kept or discarded at blocks 312 or 316, the process 300 continues at block 314 which directs the microprocessor 152 back to block 254 in the process 250 of FIG. 5 and scanning continues.

If at block 306 the result of the comparison does not meet the correspondence criterion, the microprocessor 152 is directed to block 318. Block 318 directs the microprocessor 152 to compare the successive frame n+1 with the 3D reference frame, as designated in the process 250 of FIG. 5. If at block 320, the result of the comparison meets the correspondence criterion, the microprocessor 152 is directed to block 322, which directs the microprocessor to continue scanning the object 108 with reference to the 3D reference frame. Blocks 318 and 320 thus determine that the frame n+1 corresponds to the reference frame at scanner position 204, and thus the handheld scanner 102 has been relocated by the user to resume scanning from the 3D reference frame at a scanner position 214'. Advantageously, the process 300 automatically detect that the scan should resume from the reference 3D frame without the need for user input. However, in alternative embodiments the state of the actuator button 114 or the time between frames may be monitored by the processor circuit 150 to assist in determining when the scan should resume from the reference 3D frame.

If at block 320, the result of the comparison does not meet the correspondence criterion, the microprocessor 152 is directed to block 324, which directs the microprocessor to signal a break in the frame processing. Signaling the break may involve sounding a tone to warn the operator that the scan is unable to complete successfully. Alternatively, the break may be signaled by other means, such as causing the handheld scanner 102 to vibrate, generating a visual warning, and/or displaying a highlighted 3D frame on an 3D frame display in view of the operator, for example. Block 324 also directs the microprocessor 152 to block 326, which directs the microprocessor 152 to flush the image data buffer 182 and the 3D frame buffer 184. When the break is signaled, further captured images in the image data buffer 182 and the processed 3D frames in the 3D frame buffer 184 are not able to align to the preceding frames and should thus be discarded. Block 326 also directs the microprocessor 152 to provide feedback to the operator for resuming the scan. For example, the operator may be directed to release the actuator button 114 and a representation of the object scan indicating the location of the last 3D frame that met the correspondence criterion may be displayed on the display of the computer 103. The displayed representation may include a raw image of the object from the location of the last 3D frame and/or a marker on a surface of a 3D rendering of the 3D mesh stored in the 3D mesh data store 188.

The scan resumes when the operator depresses the actuator button 114 and the process 300 continues at block 328, which directs the microprocessor 152 compare the 3D frame for the next captured image (n+2) with the last 3D frame that met the correspondence criterion (i.e. 3D frame n). If at block 330, the result of the comparison meets the correspondence criterion, the microprocessor 152 is directed to block 338, which directs the microprocessor to continue scanning the object 108 with reference to the 3D frame n.

If at block 330, the result of the comparison does not meet the correspondence criterion, the microprocessor 152 is directed to block 332, which directs the microprocessor to compare the 3D frame n+2 with the reference 3D frame. If at block 334, the result of the comparison meets the correspondence criterion, the microprocessor 152 is directed back to block 322, which directs the microprocessor to continue scanning the object 108 with reference to the 3D reference frame.

If at block 334, the result of the comparison does not meet the correspondence criterion, the microprocessor 152 is directed back to block 324, which directs the microprocessor to signal another break, and blocks 326 to 338 are repeated.

Advantageously, the process embodiments disclosed above permit scanning of the object 108 to proceed with a minimum of operator interaction with the computer 103. The system 100 automatically attempts to resume scanning at a reference position if a 3D frame does not align to a preceding 3D frame. Operator input is only required in the event where the 3D frame also does not align to the reference frame.

While specific embodiments of the invention have been described and illustrated, such embodiments should be considered illustrative of the invention only and not as limiting the invention as construed in accordance with the accompanying claims.

What is claimed:

1. A method for generating a three-dimensional (3D) scan of an object using a handheld scanner, the method comprising:

obtaining images of the object from a successive plurality of handheld scanner positions with respect to the object;

processing the images to generate a respective 3D frame for each of the plurality of handheld scanner positions, each 3D frame including data representing locations of a plurality of 3D points on a surface of the object;

designating at least one preceding 3D frame as a reference frame;

comparing each successive 3D frame with at least one preceding 3D frame;
determining whether a result of the comparison meets a correspondence criterion associated with generation of a 3D representation of the surface of the object; and
initiating a recovery process when the correspondence criterion is not met by:
comparing a subsequent 3D frame with a 3D frame preceding the 3D frame that caused initiation of the recovery process; and
if a result of the comparison does not meet the correspondence criterion, comparing at least one of the subsequent 3D frame and the 3D frame that caused initiation of the recovery process with the reference frame and resuming the scan of the object if a result of the comparison with the reference frame meets the correspondence criterion.

2. The method of claim 1 wherein determining whether the result of the comparison meets the correspondence criterion comprises determining whether 3D points associated with the 3D frame can be transformed to align with 3D points in the preceding 3D frame within a reference tolerance.

3. The method of claim 1 wherein initiating the recovery process comprises:
if a result of the comparison meets the correspondence criterion, resuming the scan of the object.

4. The method of claim 3 wherein resuming the scan of the object comprises resuming the scan without operator intervention.

5. The method of claim 2 further comprising comparing the subsequent 3D frame with the 3D frame that caused initiation of the recovery process and further comprising one of:
retaining the frame if a result of the comparison meets the correspondence criterion; and
discarding the frame if the result of the comparison does not meet the correspondence criterion.

6. The method of claim 1 wherein comparing at least one of the subsequent 3D frame and the 3D frame that caused initiation of the recovery process with the reference frame comprises comparing each of the subsequent 3D frame and the 3D frame that caused initiation of the recovery process with the reference frame.

7. The method of claim 1 wherein said designating comprises designating at least one preceding 3D frame that meets a frame quality criterion as a reference frame, wherein the frame quality criterion is based on at least one of:
the presence of topological content of the frame;
the presence of discernable features within the frame; and
a data point density within the frame.

8. The method of claim 1 wherein said designating comprises designating at least one preceding 3D frame as a reference frame in response to receiving operator input.

9. The method of claim 1 wherein said designating comprises designating a plurality of preceding 3D frames as reference frames and wherein said comparing comprises comparing at least one of the subsequent 3D frame and the 3D frame that caused initiation of the recovery process with each of the plurality of reference frames.

10. The method of claim 7 wherein designating a plurality of preceding 3D frames as reference frames comprises designating a sufficient number of 3D frames as reference frames such that when the comparison result does not meet a correspondence criterion, at least one reference frame will be in view of the handheld scanner to permit the scan of the object to resume.

11. The method of claim 1 further comprising, if the result of the comparison between the at least one subsequent 3D frame and the 3D frame that caused initiation of the recovery process with the reference frame does not meet the reference criterion, providing feedback to the operator of the handheld scanner that an operator intervention is required.

12. The method of claim 11 wherein providing feedback to the operator comprises directing the operator to re-scan a portion of the object.

13. The method of claim 12 further comprising obtaining further images of the object and processing the images to generate a further 3D frame for the re-scanned portion of the object and further comprising:
comparing the further 3D frame with a 3D frame preceding the 3D frame that caused initiation of the recovery process and if a result of the comparison meets the correspondence criterion, continuing the scan; and
comparing the further 3D frame with the reference frame and if a result of the comparison meets the correspondence criterion, continuing the scan.

14. The method of claim 11 wherein providing feedback to the operator of the handheld scanner that an operator intervention is required comprises at least one of:
generating a visual warning;
causing the handheld scanner to vibrate;
displaying a warning 3D frame on a 3D frame display in view of the operator; and
generating an audible warning.

15. The method of claim 1 wherein initiating the recovery process comprises:
generating operator feedback directing the operator to position the handheld scanner to obtain a further image from a location proximate the reference frame;
processing the image to generate a 3D frame and comparing the 3D frame with the reference frame;
determining whether a result of the comparison meets a correspondence criterion; and
resuming the scan of the object when the correspondence criterion is met.

16. The method of claim 1 further comprising
determining whether there has been an interruption in obtaining images of the object, and in response comparing a subsequent 3D frame with the reference frame and resuming the scan of the object if a result of the comparison with the reference frame meets the correspondence criterion.

17. The method of claim 16 wherein determining whether there has been an interruption in obtaining images of the object comprises determining whether an elapsed time between successive images meets an interruption criterion.

18. The method of claim 1 wherein the handheld scanner comprises a single camera and wherein obtaining images of the object comprises, for each of the plurality of handheld scanner positions:
projecting a pattern of light onto the surface of the object;
causing the camera to capture an image of the surface while being illuminated by the pattern of light;
causing the camera to capture a further image of the surface when not illuminated by the pattern of light; and
wherein comparing each successive 3D frame with at least one preceding 3D frame comprises using information provided by the further image to provide an estimate of the position of the handheld scanner for use in the comparison.

19. A system for generating a three-dimensional (3D) scan of an object, the system comprising:

a handheld scanner operable to generate images of the object from a successive plurality of handheld scanner positions with respect to the object;

a processor circuit operably configured to:
- process the images to generate a respective 3D frame for each of the plurality of handheld scanner positions, each 3D frame including data representing locations of a plurality of 3D points on a surface of the object;
- designate at least one preceding 3D frame as a reference frame;
- compare each successive 3D frame with at least one preceding 3D frame;
- determine whether a result of the comparison meets a correspondence criterion associated with generation of a 3D representation of the surface of the object; and
- initiate a recovery process when the correspondence criterion is not met by:
  - comparing a subsequent 3D frame with a 3D frame preceding the 3D frame that caused initiation of the recovery process; and
  - if a result of the comparison does not meet the correspondence criterion, comparing at least one of the subsequent 3D frame and the 3D frame that caused initiation of the recovery process with the reference frame and causing the scan of the object to resume if a result of the comparison with the reference frame meets the correspondence criterion.

20. The system of claim 19 wherein the processor circuit is operably configured to determine whether the result of the comparison meets the correspondence criterion by determining whether 3D points associated with the 3D frame can be transformed to align with 3D points in the preceding 3D frame within a reference tolerance.

21. The system of claim 19 wherein the processor circuit is operably configured to initiate the recovery process if a result of the comparison meets the correspondence criterion, causing the scan of the object to resume.

22. The system of claim 21 wherein the processor circuit is operably configured to cause the scan of the object to resume without operator intervention.

23. The system of claim 20 wherein the processor circuit is operably configured to compare the subsequent 3D frame with the 3D frame that caused initiation of the recovery process and to cause one of:
- retaining the frame if a result of the comparison meets the correspondence criterion; and
- discarding the frame if the result of the comparison does not meet the correspondence criterion.

24. The system of claim 19 wherein the processor circuit is operably configured to compare each of the subsequent 3D frames and the 3D frame that caused initiation of the recovery process with the reference frame.

25. The system of claim 19 wherein the processor circuit is operably configured to designate at least one preceding 3D frame that meets a frame quality criterion as a reference frame, wherein the frame quality criterion is based on at least one of:
- the presence of topological content of the frame;
- the presence of discernable features within the frame; and
- a data point density within the frame.

26. The system of claim 19 wherein the processor circuit is operably configured to designate at least one preceding 3D frame as a reference frame in response to receiving operator input.

27. The system of claim 19 wherein the processor circuit is operably configured to designate the at least one preceding 3D frame by designating a plurality of preceding 3D frames as reference frames and to compare at least one of the subsequent 3D frame and the 3D frame that caused initiation of the recovery process with each of the plurality of reference frames.

28. The system of claim 25 wherein the processor circuit is operably configured to designate the plurality of preceding 3D frames as reference frames by designating a sufficient number of 3D frames as reference frames such that when the comparison result does not meet a correspondence criterion, at least one reference frame will be in view of the handheld scanner to permit the scan of the object to resume.

29. The system of claim 19 wherein, if the result of the comparison between the at least one subsequent 3D frame and the 3D frame that caused initiation of the recovery process with the reference frame does not meet the reference criterion, the processor circuit is operably configured to provide feedback to the operator of the handheld scanner that a operator intervention is required.

30. The system of claim 29 wherein the processor circuit is operably configured to provide feedback to the operator by directing the operator to re-scan a portion of the object.

31. The system of claim 30 wherein the handheld scanner is operable to generate further images of the object and the processor circuit is operably configured to process the images to generate a further 3D frame for the re-scanned portion of the object and to:
- compare the further 3D frame with a 3D frame preceding the 3D frame that caused initiation of the recovery process and if a result of the comparison meets the correspondence criterion, continue the scan; and
- compare the further 3D frame with the reference frame and if a result of the comparison meets the correspondence criterion, continue the scan.

32. The system of claim 29 wherein the processor circuit is operably configured to provide feedback to the operator of the handheld scanner that an operator intervention is required by at least one of:
- generating a visual warning;
- causing the handheld scanner to vibrate;
- displaying a warning 3D frame on a 3D frame display in view of the operator; and
- generating an audible warning.

33. The system of claim 19 wherein the processor circuit is operably configured to
- generate operator feedback directing the operator to position the handheld scanner to generate a further image from a location proximate the reference frame;
- process the image to generate a 3D frame and comparing the 3D frame with the reference frame;
- determine whether a result of the comparison meets a correspondence criterion; and
- resume the scan of the object when the correspondence criterion is met.

34. The system of claim 19 wherein the processor circuit is operably configured to
- determine whether there has been an interruption in generating images of the object, and in response comparing a subsequent 3D frame with the reference frame and resuming the scan of the object if a result of the comparison with the reference frame meets the correspondence criterion.

35. The system of claim 34 wherein the processor circuit is operably configured to determine whether there has been an interruption in generating images of the object by determining whether an elapsed time between successive images meets an interruption criterion.

36. The system of claim 19 wherein the handheld scanner comprises a single camera, and wherein the single camera is operably configured to generate images of the object from the successive plurality of handheld scanner positions with respect to the object by:
   projecting a pattern of light onto the surface of the object;
   capturing an image of the surface while being illuminated by the pattern of light;
   capturing a further image of the surface when not illuminated by the pattern of light; and
   wherein the processor circuit is operably configured to compare each successive 3D frame with at least one preceding 3D frame by using information provided by the further image to provide an estimate of the position of the handheld scanner for use in the comparison.

* * * * *